US011589452B2

(12) United States Patent
Ryding et al.

(10) Patent No.: US 11,589,452 B2
(45) Date of Patent: Feb. 21, 2023

(54) ION BEAM FILTER FOR A NEUTRON GENERATOR

(71) Applicant: Neutron Therapeutics, Inc., Danvers, MA (US)

(72) Inventors: Geoffrey Ryding, Manchester, MA (US); Takao Sakase, Rowley, MA (US); William H. Park, Marblehead, MA (US); Theodore H. Smick, Gloucester, MA (US)

(73) Assignee: Neutron Therapeutics, Inc., Danvers, MA (US)

( * ) Notice: Subject to any disclaimer, the term of this patent is extended or adjusted under 35 U.S.C. 154(b) by 915 days.

(21) Appl. No.: 16/640,218

(22) PCT Filed: May 5, 2017

(86) PCT No.: PCT/US2017/031262
§ 371 (c)(1),
(2) Date: Feb. 19, 2020

(87) PCT Pub. No.: WO2017/196659
PCT Pub. Date: Nov. 16, 2017

(65) Prior Publication Data
US 2020/0196428 A1    Jun. 18, 2020

Related U.S. Application Data

(60) Provisional application No. 62/335,233, filed on May 12, 2016.

(51) Int. Cl.
*A61N 5/10* (2006.01)
*H05H 3/06* (2006.01)
(Continued)

(52) U.S. Cl.
CPC ............. *H05H 3/06* (2013.01); *A61N 5/1077* (2013.01); *A61N 5/1078* (2013.01);
(Continued)

(58) Field of Classification Search
CPC ...... A61N 5/10; A61N 5/1077; A61N 5/1078; A61N 5/1079; A61N 2005/1085;
(Continued)

(56) References Cited

U.S. PATENT DOCUMENTS 4,090,086 A * 5/1978 Granberg ................. H05H 6/00
376/116
4,119,858 A * 10/1978 Granberg ................. H05H 3/06
376/116
(Continued)

FOREIGN PATENT DOCUMENTS

CN       203057673       7/2013
JP       2011-33512      2/2011
(Continued)

OTHER PUBLICATIONS

Sergey Taskaev et al., Neutron Source Based on Vacuum Insulated Tandem Accelerator and Lithium Target, Biology vol. 10(5)350, Apr. 21, 2021. (Year: 2021).*
Satoshi Nakamura et al., Neutron flux evaluation model provided in the accelerator-based boron neutron capture therapy system employing a solid-state lithium target, Scientific Reports 11, 8090, Apr. 13, 2021. (Year: 2021).*
(Continued)

*Primary Examiner* — Allen C. Ho
(74) *Attorney, Agent, or Firm* — DLA Piper LLP (US)

(57) ABSTRACT

The present disclosures relates to an ion beam assembly where a relatively small deflection angle (approximately 15° from the center of the beam line) is used in conjunction with two beam dumps located on either side of the beam. In some embodiments, the combination of the two beam dumps and the magnet assembly can provide an ion beam filter. In some (Continued)

embodiments, the resulting system provides a smaller, safer and more reliable ion beam. In some embodiments, the ion beam can be a proton beam.

22 Claims, 2 Drawing Sheets

(51) Int. Cl.
*G21G 1/10* (2006.01)
*G21K 1/00* (2006.01)
*G21K 5/04* (2006.01)
*G21K 5/08* (2006.01)

(52) U.S. Cl.
CPC .............. *A61N 5/1079* (2013.01); *G21G 1/10* (2013.01); *G21K 1/00* (2013.01); *G21K 5/04* (2013.01); *G21K 5/08* (2013.01); *A61N 2005/109* (2013.01); *A61N 2005/1087* (2013.01); *A61N 2005/1095* (2013.01)

(58) Field of Classification Search
CPC ...... A61N 2005/1087; A61N 2005/109; A61N 2005/1095; H05H 3/06
USPC ...................... 250/493.1, 496.1, 498.1, 503.1
See application file for complete search history.

(56) References Cited

U.S. PATENT DOCUMENTS

| 7,236,566 | B2* | 6/2007 | Gibson | G01N 23/207 378/85 |
| 8,148,922 | B2* | 4/2012 | Cleland | H05H 5/00 315/501 |
| 8,633,458 | B2* | 1/2014 | Smick | H01J 37/3171 250/492.1 |
| 10,098,218 | B2* | 10/2018 | Yamamoto | H05H 7/001 |
| 10,462,893 | B2* | 10/2019 | Park, Jr. | G21G 4/02 |
| 11,024,437 | B2* | 6/2021 | Park, Jr. | H05H 3/06 |
| 2006/0140343 | A1 | 6/2006 | Gibson et al. | |
| 2014/0130741 | A1 | 5/2014 | Smick et al. | |

FOREIGN PATENT DOCUMENTS

| KR | 10-2007-0082124 | 8/2007 |
| WO | 2014/046641 | 3/2014 |
| WO | 2016/060867 | 4/2016 |

OTHER PUBLICATIONS

M. R. Cleland and B. P. Offermann, The Dynagen IV—A Compact High-Intensity Neutron Source, Nuclear Instrumentsand Methods 145 (1977) 41-47 (Year: 1977).*

* cited by examiner

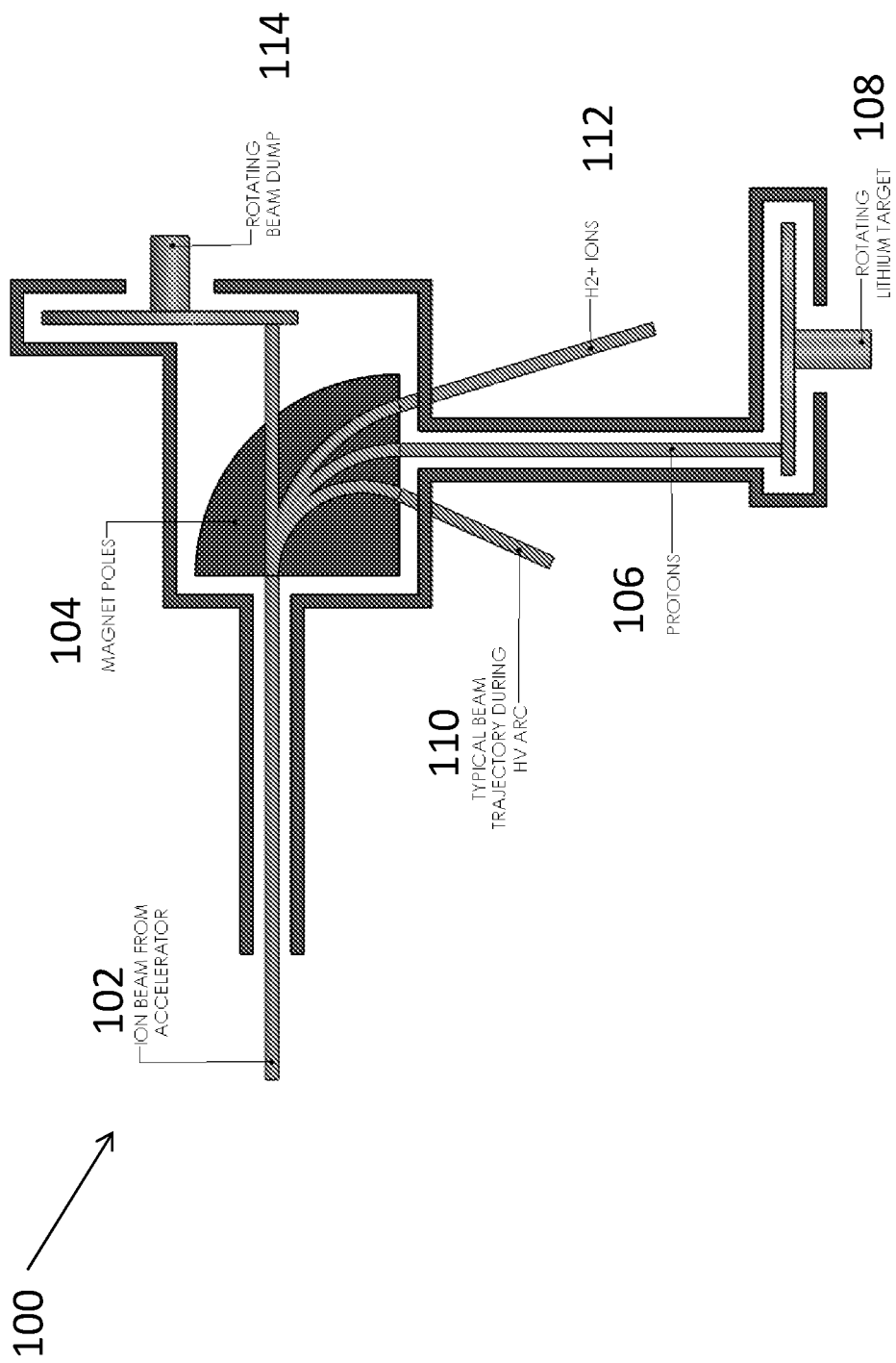
FIG 1. SCHEMATIC OF 90° FILTER MAGNET

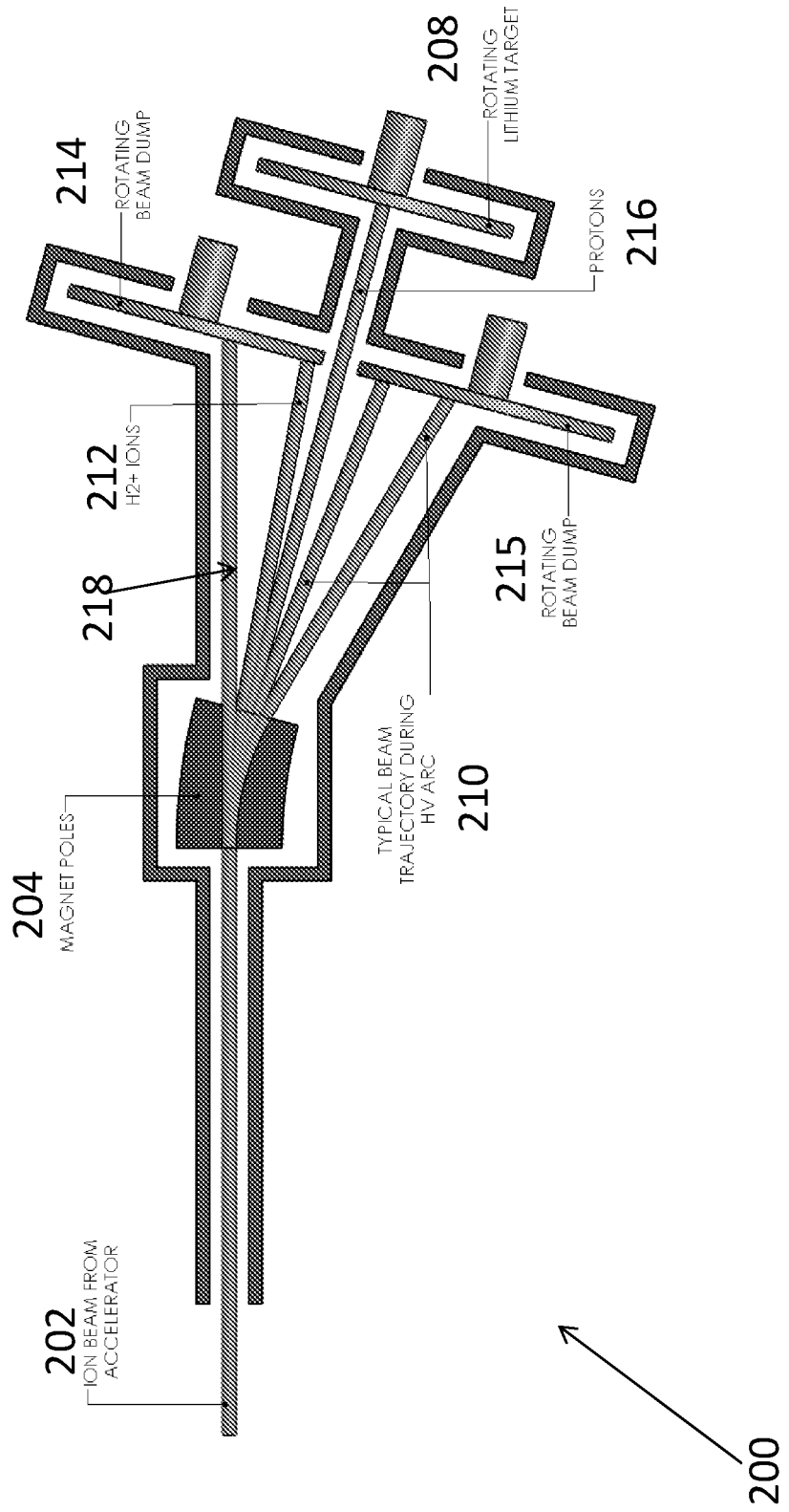

ION BEAM FILTER FOR A NEUTRON GENERATOR

CROSS-REFERENCE TO RELATED APPLICATIONS

This application is a National Stage of PCT/US2017/031262, filed May 5, 2017, which claims priority to and the benefit of U.S. Provisional Patent Application No. 62/335,233 filed on May 12, 2016, the disclosure of which is incorporated herein by reference in its entirety.

FIELD OF THE DISCLOSURE

The present disclosure relates to methods and systems for generating neutrons using a system having an ion beam filter.

BACKGROUND

Ion beams, produced by a particle accelerator, or through other means, can be used to create neutrons by bombarding a neutron producing target with the ion beam. The neutrons generated can then be used for procedures, for example, Boron Neutron Capture Therapy (BNCT). However, the ion beam, or proton beam, in some systems, is high-power and when not properly controlled, can cause damage to the systems within which it is used.

SUMMARY

The present disclosures relates to an ion beam assembly where a relatively small deflection angle (approximately 15° from the center of the beam line) is used in conjunction with two beam dumps located on either side of the beam. The combination of the two beam dumps and the magnet assembly can provide an ion beam filter. The resulting system provides a smaller, safer and more reliable ion beam. In some embodiments, the ion beam can be a proton beam.

The present disclosure relates to a system for generating neutrons. The system can have an ion source configured to generate an ion beam, and a magnet system configured to deflect the ion beam by a first angle from the center of the ion beam. The system can have a rotating neutron source disposed at the first angle from the center of the beam and configured to receive the ion beam and generate a neutron flux. The system can have a first rotating beam dump configured to receive a first plurality of ions from the ion beam. The system can have a second rotating beam dump disposed at a second angle from the center of the ion beam and configured to receive a second plurality of ions from the ion beam, wherein the second angle is larger than the first angle.

In some embodiments, the ion beam can be a proton beam, a deuterium beam, or a combination thereof.

In some embodiments, the first angle can be between 0 degree and 45 degrees. In some embodiments, the first angle can be substantially 15 degrees.

In some embodiments, the first rotating beam dump and the rotating neutron source can have internal cooling channels for water cooling.

In some embodiments, the first rotating beam dump can be graphite, aluminum, or a combination thereof. In some embodiments, the second rotating beam dump can be graphite. In some embodiments, the rotating neutron source can be lithium.

In some embodiments, the first rotating beam dump can have one or more openings and a first beam detector can be disposed behind the first rotating beam dump for monitoring a profile of the ion beam. In some embodiments, the rotating neutron source can have one or more openings and a second beam detector can be disposed behind the rotating neutron source for monitoring a profile of the ion beam.

In some embodiments, the first rotating beam dump can be disposed on a straight-through path of the ion beam.

The present disclosure also relates to a method for generating neutrons. The method can include generating an ion beam with an ion source, and deflecting the ion beam by a first angle from the center of the ion beam with a magnet system. The method can include receiving the ion beam and generating a neutron flux with a neutron source which can be disposed at the first angle from the center of the ion beam. The method can include receiving a first plurality of ions from the ion beam with a first rotating beam dump. The method can include receiving a second plurality of ions from the ion beam with a second rotating beam dump which can be disposed at a second angle from the center of the ion beam, wherein the second angle is larger than the first angle.

In some embodiments, the method can include generating a proton beam, a deuterium beam, or a combination thereof, as the ion beam.

In some embodiments, the first angle can be between 0 degree and 45 degrees. In some embodiments, the first angle can be substantially 15 degrees.

In some embodiments, the method can include cooling the first rotating beam dump and the rotating neutron source by passing water through internal cooling channels in the first rotating beam dump and the rotating neutron source.

In some embodiments, the first rotating beam dump can be graphite, aluminum, or a combination thereof. In some embodiments, the second rotating beam dump can be graphite. In some embodiments, the rotating neutron source can be lithium.

In some embodiments, the method can include passing the ion beam through one or more openings on the first rotating beam dump and receiving the ion beam by a first beam detector behind the first rotating beam dump to monitor a profile of the ion beam. In some embodiments, the method can include passing the ion beam through one or more openings on the rotating neutron source and receiving the ion beam by a second beam detector behind the rotating neutron source to monitor a profile of the ion beam.

In some embodiments, the method can include disposing the first rotating beam dump on a straight-through path of the ion beam.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 1 shows a schematic of a beam transport system based on a 90° magnetic beam deflection, according to some embodiments of the present disclosure.

FIG. 2 shows a schematic of a beam transport system based on a 15° deflection/analysis of the beam emerging from the accelerator, according to some embodiments of the present disclosure.

DETAILED DESCRIPTION

In the following description, numerous specific details are set forth regarding the systems and methods of the disclosed subject matter and the environment in which such systems, methods and media may operate, etc., in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the examples provided below are exemplary, and that it is contemplated that there are other systems and methods that are within the scope of the disclosed subject matter.

The described neutron generator is based on the $^7$Li(p,n)$^7$Be reaction. The neutrons are generated when a proton beam with an energy in the range between 1.882 MeV (reaction threshold) and approximately 2.6 MeV collides with a lithium target. The target is surrounded by a neutron energy moderator which eliminates the high energy neutrons produced in the reaction and leads to a typical neutron energy spectrum in the range 0.5 eV to 10 keV. These epithermal neutrons are well suited for use in BNCT.

The high energy protons can be produced using a number of accelerator technologies including but not limited to Electrostatic ('Single-ended' or 'Tandem'), linear accelerator, radio frequency quadrupole, and cyclotron. Some accelerator architectures can produce high-power (~100 kW) high-current (~40 mA) proton beams specifically for use in BNCT. These accelerators can be used with lithium target technology capable of handling the high power (~100 kW) proton beams (see U.S. Pat. No. 11,024,437 B2 issued on Jun. 1, 2021, Neutron Target for Boron Neutron Capture Therapy, filed May 5, 2016, the entire contents of which are hereby incorporated by reference).

Transporting this high power beam from the accelerator to the lithium target can present a number of technical challenges as discussed below.

First, the ion beam emerging from a proton accelerator typically contains unwanted ion species, other than the protons, which do not contribute to the production of neutrons. These may include ions produced in the ion source such as $H_2^+$, $H_3^+$, $N^+$, $O^+$, $OH^+$, etc. which have not been filtered out. These unwanted ions can be produced as secondary ions when the primary beam collides with residual gas atoms or molecules in the accelerator tube and can also be accelerated towards the target.

Ion beams containing ions of different mass or energy can be readily filtered by passing the beam through a sector magnet. This technique is used in both isotope separator and mass spectrometer systems and exploits the fact that the radius of curvature of an ion traversing a magnetic field depends on the magnetic field according to the equation:

$$R\alpha H^{-1}e^{-i}E^{1/2}M^{1/2}$$

where R is the radius of curvature, H is the magnetic field, e is the charge on the ion, M is the ion mass and E is the ion energy.

For a given deflection geometry, the required ion species can be readily selected and directed to the target by adjusting the magnetic field to the appropriate value.

In the case of high-power ~100 kW beams, it should be noted that even small unwanted fractions of the primary beam can have significant power and are capable of doing damage to a beam handling system. For example, the fraction of $H_2^+$ ions emerging from an ion source can often be ~10% of the total beam output and will result in a beam power of ~10 kW after acceleration.

Second, if the high-voltage section of the accelerator is perturbed as a result of an arc in the accelerator tube or the high voltage insulating structure, the proton beam energy can be temporarily reduced and the beam can be deflected with a smaller radius, directing it away from its intended path in the sector magnet. In so doing, the beam may strike regions of the system that are not capable of handling the high power. 'Structure' here can refer to any part of the high-voltage apparatus (accelerator column) other than the tube (which is only the accelerator electrodes and intervening insulators, a hermetically sealed enclosure separating vacuum from pressurized sulfur hexafluoride ("SF6") gas). Accordingly, the structure can include the power supplies, drive shafts, alternators and any structural elements that physically support these items. In some embodiments, the structure can be immersed in the SF6.

Third, operator error or errors in the control system could inadvertently misdirect the beam into regions of the system susceptible to damage.

Fourth, the ability to add neutron absorbing materials (for example concrete) to prevent direct 'line of sight' between the neutron generating lithium on the target and the proton accelerator is a further requirement of the beam transport system. This would be significantly harder to achieve with a transport system that has no bend in its beamline FIG. 1 shows a simple schematic of a beam transport system 100 based on a 90° magnetic beam deflection. In some embodiments, beam transport system 100, during operation, can include an ion beam from an accelerator 102, a magnet system 104, a beam of protons 106, a rotating lithium target 108, and a rotating beam dump 114. FIG. 1 also shows a typical beam trajectory during a high-voltage arc 110 and an $H_2^+$ beam 112. The entire system can be disposed within a vacuum chamber.

In a normal operating sequence beam 102 is first tuned to the desired intensity at the straight through rotating beam dump 114 with the deflector magnet system 104 turned off. The deflector (analyzer) magnet system 104 is then turned on so that the beam of protons 106 is directed, at in this example, a 90° angle, towards rotating lithium target 108. In some embodiments, the ion source can be turned off during this process, often referred to as beam sweeping, so as to avoid damage to the walls of the vacuum chamber.

FIG. 2 shows a simple schematic of a beam transport system 200 based on a 15° deflection/analysis of the beam emerging from the accelerator. Beam transport system 200, shown in FIG. 2, can include an ion beam 202, a magnet system 204, a rotating lithium target 208, a first rotating beam dump 214, a second rotating beam dump 215. FIG. 2 also shows a typical beam trajectory during a high voltage arc 210 and an $H_2^+$ beam 212. First rotating beam dump 214, shows both 'straight through' beam tuning position 218 and $H_2^+$ position during operation. Second rotating beam dump 215 shows two typical beam trajectories during high voltage arcs 210 which represent two different degrees of voltage collapse. These trajectories 210 represent the typical range of high-power beams that could exist during an arc. The beam angle could be somewhat larger than 15°, but it can be difficult to maintain the desired optical properties (for example, no waists). The beam angle could be somewhat smaller than 15 but it becomes more difficult to avoid line of sight from target to accelerator.

As shown in FIG. 2, in some embodiments, two rotating beam dumps 214, 215 have been added. The first beam dump 214 can be used to tune the system in the 'straight through' position 218 when the deflector magnet is turned off and it is designed to handle the full beam power. The first beam dump 214 also can be used to collect $H_2^+$ beam 212 and any additional heavy ion contaminants during normal operation. The second beam dump 215 can collect any beams that are deflected more than 15° which may occur during voltage breakdown of one or more of the high voltage supplies in the accelerator. In some embodiments, the first rotating beam dump 214 can be similar in diameter with the rotating lithium target 208. In some embodiments, the first rotating beam dump 214 can be larger in diameter than the rotating lithium target 208. In some embodiments, the second rotating beam dump 215 can be much smaller in diameter than the first beam dump 214 and the rotating lithium target 208. In one embodiment, the rotating lithium target 208, the first rotating beam dump 214, and the second rotating beam dump 215 can have diameters of 1.2 m, 1.5 m, and 0.6 m, respectively.

These beam dumps 214, 215 can be water cooled spinning disks as used in the lithium target described in U.S. Pat. No. 11,024,437 B2 issued on Jun. 1, 2021, Neutron Target for Boron Neutron Capture Therapy, filed May 5, 2016, the entire contents of which are hereby incorporated by reference. In some embodiments, graphite disks can be used which can dissipate the beam power by radiation to the water cooled walls of the vacuum chamber. In some embodiments, the second rotating beam dump 215 can be a graphite disk cooled by radiative cooling, while the first rotating beam dump 214 and the rotating lithium target 208 can have internal cooling channels for water cooling. In some embodiments, the first rotating beam dump 214 can have a different construction (i.e., cooling channels, shape and number of petals, diameter and materials) compared to the rotating lithium target 208. In some embodiments, the first rotating beam dump 214 can have an array of openings and a first beam detector can be disposed behind the first rotating beam dump 214, so that the profile of the ion source can be determined. In some embodiments, the rotating lithium target 208 can include an array of openings and a second beam detector can be disposed behind the rotating neutron source, so that the profile of the ion source can be determined.

The first rotating beam dump 214 can include materials chosen to limit the gamma and neutron radiation hazard produced by the full power beam impinging on the first rotating beam dump 214 during setup operations and the filtered molecular beam impinging on the first rotating beam dump 214 during normal operation. In some embodiments, the first rotating beam dump 214 can be graphite if the ion source is a proton beam. In some embodiments, the first rotating beam dump 214 can be aluminum if the ion source is a deuterium beam.

With the configuration shown in FIG. 2 it can be seen that the high-power beam 202 from the accelerator (~100 kW) can be safely contained during operation. Beam(s) can only strike the lithium target disk 208 or the first rotating beam dump 214 which are designed to handle the full beam power.

Finally, it should be noted that the magnetic deflection angle avoids a direct line of sight from the Li target region to the accelerator. This architecture enables the strategic placing of neutron radiation shields (concrete blocks, plastic, steel, lead etc.) so that the problem of neutron radiation damage to the accelerator is prevented.

The described system can have the following advantages: (1) smaller (because of the smaller angle), simpler magnet; (2) more convenient, linear layout for facility design and (3) the beam dumps can also function as beam limiting apertures, precisely defining the area on the primary target where beam may strike. This third advantage can prevent any stray beam from reaching unprotected regions of the system. Compared to a large angle system that includes dedicated beam dumps for this purpose, there are fewer beam dumps required in the small angle case.

The described system can also result in improved beam optics; in particular a 15° deflector may eliminate the need for waists in the beamline A waist in a beam line is a place where the beam crosses over itself and therefore becomes highly focused. The presence of a waist is a hazard to the adjacent beamline structures, as well as the primary target. This is because the waist can inadvertently be directed onto components further down the beamline due to instability, magnet failure, operator error or other off-normal circumstances. In the case of a 15° beamline with no waists, the probability of this failure mode is greatly reduced.

There has thus been outlined the features of the disclosed subject matter in order that the detailed description thereof that follows may be better understood, and in order that the present contribution to the art may be better appreciated.

In this respect, before explaining at least one embodiment of the disclosed subject matter in detail, it is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

What is claimed is:

1. A system for generating neutrons comprising:
   an ion source configured to generate an ion beam;
   a magnet system configured to deflect the ion beam by a first angle from a center of the ion beam;
   a rotating neutron source disposed at the first angle from the center of the ion beam and configured to receive the ion beam and generate a neutron flux;
   a first rotating beam dump configured to receive a first plurality of ions from the ion beam; and
   a second rotating beam dump disposed at a second angle from the center of the ion beam and configured to receive a second plurality of ions from the ion beam, wherein the second angle is larger than the first angle.

2. The system of claim 1, wherein the ion beam comprises a proton beam, a deuterium beam, or a combination thereof.

3. The system of claim 1, wherein the first angle is between 0 degree and 45 degrees.

4. The system of claim 3, wherein the first angle is substantially 15 degrees.

5. The system of claim 1, wherein the first rotating beam dump and the rotating neutron source comprise internal cooling channels for water cooling.

6. The system of claim 1, wherein the first rotating beam dump comprises graphite, aluminum, or a combination thereof.

7. The system of claim 1, wherein the second rotating beam dump comprises graphite.

8. The system of claim 1, wherein the rotating neutron source comprises lithium.

9. The system of claim 1, further comprising one or more openings on the first rotating beam dump and a first beam detector behind the first rotating beam dump for monitoring a profile of the ion beam.

10. The system of claim 1, further comprising one or more openings on the rotating neutron source and a second beam detector behind the rotating neutron source for monitoring a profile of the ion beam.

11. The system of claim 1, wherein the first rotating beam dump is disposed on a straight-through path of the ion beam.

12. A method for generating neutrons comprising:
generating an ion beam with an ion source;
deflecting the ion beam by a first angle from a center of the ion beam with a magnet system;
receiving the ion beam and generating a neutron flux with a rotating neutron source disposed at the first angle from the center of the ion beam;
receiving a first plurality of ions from the ion beam with a first rotating beam dump; and
receiving a second plurality of ions from the ion beam with a second rotating beam dump disposed at a second angle from the center of the ion beam, wherein the second angle is larger than the first angle.

13. The method of claim 12, further comprising generating a proton beam, a deuterium beam, or a combination thereof, as the ion beam within the ion source.

14. The method of claim 12, wherein the first angle is between 0 degree and 45 degrees.

15. The method of claim 14, wherein the first angle is substantially 15 degrees.

16. The method of claim 12, further comprising cooling the first rotating beam dump and the rotating neutron source by passing water through internal cooling channels in the first rotating beam dump and the rotating neutron source.

17. The method of claim 12, wherein the first rotating beam dump comprises graphite, aluminum, or a combination thereof.

18. The method of claim 12, wherein the second rotating beam dump comprises graphite.

19. The method of claim 12, wherein the rotating neutron source comprises lithium.

20. The method of claim 12, further comprising:
passing the ion beam through one or more openings on the first rotating beam dump; and
receiving the ion beam by a first beam detector behind the first rotating beam dump to monitor a profile of the ion beam.

21. The method of claim 12, further comprising:
passing the ion beam through one or more openings on the rotating neutron source; and
receiving the ion beam by a second beam detector behind the rotating neutron source to monitor a profile of the ion beam.

22. The method of claim 12, further comprising disposing the first rotating beam dump on a straight-through path of the ion beam.

* * * * *